US011154409B2

(12) United States Patent
Expósito Ollero et al.

(10) Patent No.: US 11,154,409 B2
(45) Date of Patent: Oct. 26, 2021

(54) DEVICE FOR THE EXO-PROSTHETISATION OF LIMBS AND OTHER PERCUTANEOUS APPLICATIONS

(71) Applicants: UNIVERSITAT POLITÈCNICA DE VALÈNCIA, Valencia (ES); UNIVERSITAT DE VALÈNCIA, Valencia (ES); FUNDACIÓN PARA LA INVESTIGACIÓN DEL HOSPITAL CLÍNICO DE LA COMUNIDAD VALENCIANA (INCLIVA), Valencia (ES)

(72) Inventors: José Expósito Ollero, Valencia (ES); Ana Vallés Lluch, Valencia (ES); José Albelda Vitoria, Valencia (ES); Juan Victor Hoyos Fuentes, Valencia (ES); Antonio Silvestre Muñoz, Valencia (ES)

(73) Assignees: UNIVERSITAT POLITÉCNICA DE VALÈNCIA, Valencia (ES); UNIVERSITAT DE VALÈNCIA, Valencia (ES); FUNDACIÓN PARA LA INVESTIGACIÓN DEL HOSPITAL CLÍNICO DE LA COMUNIDAD VALENCIANA (INCLIVA), Valencia (ES)

( * ) Notice: Subject to any disclaimer, the term of this patent is extended or adjusted under 35 U.S.C. 154(b) by 189 days.

(21) Appl. No.: 16/333,107

(22) PCT Filed: Aug. 1, 2017

(86) PCT No.: PCT/ES2017/070562
§ 371 (c)(1),
(2) Date: Jun. 25, 2019

(87) PCT Pub. No.: WO2018/050934
PCT Pub. Date: Mar. 22, 2018

(65) Prior Publication Data
US 2019/0328554 A1 Oct. 31, 2019

(30) Foreign Application Priority Data
Sep. 19, 2016 (ES) .............................. ES201631218

(51) Int. Cl.
*A61F 2/80* (2006.01)
*A61F 5/449* (2006.01)
(Continued)

(52) U.S. Cl.
CPC .................. *A61F 2/80* (2013.01); *A61F 2/78* (2013.01); *A61F 5/449* (2013.01); *A61F 2002/5021* (2013.01); *A61F 2002/7887* (2013.01)

(58) Field of Classification Search
CPC .... A61F 2/80; A61F 2/78; A61F 5/449; A61F 2002/5021; A61F 2002/7887
See application file for complete search history.

(56) References Cited

U.S. PATENT DOCUMENTS

| 4,158,895 A | 6/1979 | Reswick et al. | |
| 6,900,055 B1 * | 5/2005 | Fuller | A61P 5/00 435/395 |

(Continued)

FOREIGN PATENT DOCUMENTS

| EP | 2907484 A1 | 8/2015 |
| ES | 2257627 T3 | 8/2006 |
| WO | 2014015303 A1 | 1/2014 |

*Primary Examiner* — Jerrah Edwards
*Assistant Examiner* — Aren Patel
(74) *Attorney, Agent, or Firm* — Hayes Soloway PC

(57) ABSTRACT

A percutaneous collar is made up of a central rigid ring and a flexible mesh inside a microporous silicone disc. The volume of the disc has a three-dimensional network of interconnected micropores forming microchannels connect-
(Continued)

ing both external faces of the disc through the external micropores to the internal flexible mesh wherein the flexible mesh is formed by crossed longitudinal and radial elements or plates which form a plurality of holes.

11 Claims, 2 Drawing Sheets

(51) Int. Cl.
*A61F 2/78* (2006.01)
*A61F 2/50* (2006.01)

(56) References Cited

U.S. PATENT DOCUMENTS

| | | | |
|---|---|---|---|
| 2007/0060891 A1* | 3/2007 | Skiera | A61F 2/78 604/175 |
| 2014/0195002 A1* | 7/2014 | Bachus | A61F 2/2814 623/23.44 |
| 2014/0228973 A1* | 8/2014 | Porter | A61F 2/2814 623/33 |
| 2015/0289978 A1* | 10/2015 | Fitzpatrick | A61F 2/78 623/23.5 |
| 2016/0199201 A1* | 7/2016 | Weiss | A61F 2/78 623/32 |

\* cited by examiner

DEVICE FOR THE EXO-PROSTHETISATION OF LIMBS AND OTHER PERCUTANEOUS APPLICATIONS

CROSS-REFERENCE TO RELATED APPLICATIONS AND PRIORITY

This patent application claims priority from International Patent Application No. PCT/ES2017/070562 filed Aug. 1, 2017, which claims the benefit of ES Patent Application No. P201631218 filed Sep. 19, 2016. Each of these patent applications are herein incorporated by reference in their entirety.

TECHNICAL FIELD

The present invention relates to a device intended to create the bond of the soft tissues (dermal and adipose) in exo-prosthetisation applications for limbs, that is, in order to fasten an external prosthetic to the inside of the limb by establishing a tight and stable seal between the soft distal tissues and the device of the invention. The main element thereof is a percutaneous collar which offers advantages over the elements known in the state of the art.

Alternatively, the device can be used in other percutaneous applications such as ostomies (cystostomies, colostomies, or any other method of derivation) as well as gastric applications by adapting it to a catheter with threading in the vicinity of the stoma instead of an intramedullary rod.

This system is for application in the medical and veterinary field.

STATE OF THE ART

In the state of the art documents ES2257627T3 and US2007060891A1 are known which respectively relate to a device for fastening prosthesis to a finger, and to percutaneous collars.

Silicone compounds have been used by some of the systems in the preparation of dermal collars, for example, the EEFP system proposes the use of this material by way of internal layers of silicone adhered to other external layers of metal wool; other systems propose collars made of titanium or tantalum coated in silicone forming a rigid structure. However, these systems either put the titanium wool and the skin in direct contact, or they end up fastening the soft tissues to stiff titanium rings.

Some of the current systems proposed, which are intended to favour the adhesion of the dermal tissue to the implant by creating the percutaneous seal, are limited to extending the rigid intramedullary rod, made of titanium or another metal alloy.

This extension through the stoma directly creates the implant-dermis bond, whether it be through a microporous surface which favours internal growth, or a smooth surface which prevents the accumulation of microorganisms.

Other systems propose the use of a rigid percutaneous collar made of carbon (UA system), or a distal washer made of perforated titanium (ITAP system), or microporous dome-shaped percutaneous collars made of titanium or tantalum. These systems, in addition to carrying out the main function of creating the bond of the dermal tissue with the implant, are designed with the intention to support the soft distal tissues by removing a portion of these tissues (adipose tissue and residual musculature) and by restricting the freedom of movement of the structure formed by the dermal tissue, adipose tissue and muscular tissue of the distal area.

The document closest to the invention, US2007060891, describes an exo-prosthetisation device of the type formed by a carrier element of a percutaneous collar with an end projecting from the dermis, according to FIG. 1 of this document. The percutaneous collar is formed by a planar central stiff ring bound to the carrier end and the disc is made with a flexible material comprising pores on the outer portion thereof. This document generically details that the planar part can be made in a mesh structure, without specifying the geometry thereof. The mesh-type structure enables the elasticity of the planar part to be modified. The pores of the outer portion promote cellular adhesion only on the external surface and prevent the anchoring of the adipose tissue.

OBJECT OF THE INVENTION

The problem solved by the present invention is finding a device for exo-prosthetisation which promotes not only the adhesion of the tissue to the external surface, as described in US2007060891, but also to stimulate the internal proliferation of the precursor cells of new scar tissue in the entire internal volume of the collar, that is, creating a larger amount of fibrous scar tissue which generates a denser and stronger protective barrier against infectious agents.

Another problem solved by the invention is that of preventing tearing in the stoma and reducing marsupialisation.

The solution found by the inventors is a flexible disc which covers an internal mesh, the flexible disc comprising pores on the outer portion thereof and the internal volume thereof is formed by a three-dimensional network of interconnected micropores which connect both external faces of the disc, through the external pores, with the internal mesh, wherein the mesh is made up of crossed longitudinal and radial elements or plates with a plurality of holes. Additionally, the internal mesh can be surrounded by a series of ordered channels which run along the geometry of the entire internal mesh. These ordered channels connect to the 3D network of interconnected micropores and through this network with the pores of the surfaces. Thus, a larger adhesive surface is provided for the internal mesh by being surrounded in the entire surface thereof by the ordered channels wherein the cells will be housed.

The interconnected micropores have a cell size, that is, from tens of microns to hundreds of microns, in order to house cells and so these can migrate between the micropores.

BRIEF DESCRIPTION OF THE INVENTION

The invention consists of a device intended to create the bond of the soft tissues (dermal and adipose) in applications of exo-prosthetisation of limbs and other percutaneous applications according to the claims. The different embodiments thereof solve the problems in the state of the art.

The percutaneous collar proposed as part of the device is a component that is completely microporous and flexible (made up of silicone or similar) which favours the internal growth and adhesion of the distal soft tissues (dermal and adipose) to an internal flexible mesh or grate made of titanium or a polymeric material (without coating or coated with bioactive material favouring cellular adhesion) or a mesh with similar characteristics, maintaining as much as possible the normal physiological structure formed by the dermal tissue, the adipose tissue and the muscle tissue.

The collar of the device adopts a structure by which the internal flexible mesh or grate, intended to create the bond with the distal soft tissues, remains protected inside the completely microporous, flexible and soft compound in contact with the soft tissues (cutaneous and subcutaneous tissue), which run through the microchannels to the inside wherein the flexible mesh or grate is found.

The collar carries out the function of supporting the soft tissues adjacent to the implant-dermis bond area with the goal of preventing chafings and irritations in the stoma, while giving the collar-dermis interface enough elasticity to enable the relative movement of the tissues preventing tears in the stoma.

The device was developed after studying the structure formed by the distal soft tissues and how the forces are transmitted through the existing fascias between the different tissues. The device of the invention attempts to reduce the adverse effects of avulsion or tearing (which generate deficient bonds with the resulting occurrence of infections) due to the adhesion of the distal soft tissues to rigid surfaces in the areas of the body where there is greater relative movement between the tissues and to the resection of a portion of these soft tissues responsible for dissipating or shielding from the tearing tensions. Therefore, this device, by being a flexible component which maintains the physiological structure of the distal soft tissues (dermal and adipose tissue) enables shielding from the tearing tensions generated in the stoma by distributing them in a more homogeneous manner.

Specifically, the device for the exo-prosthetisation of limbs and other percutaneous applications is of the type formed by a carrier element, which can be a rod with a surrounding support at an osteotomy level which is fastened to a bone (generally in the intramedullary area) and comprises an element projecting from the epidermis in order to fasten the prosthesis. The carrier element could also be a catheter prepared to carry a percutaneous collar in the stoma area. It is especially characterised in that it comprises a percutaneous collar formed by a central rigid ring and a flexible mesh inside a disc with an internal 3D microporous structure which can be made of silicone or another polymer with similar characteristics. The disc comprises a 3D network of microchannels formed by micropores interconnected to each other. The network of microchannels is directly connected to the internal mesh or through a main network of ordered channels which surround the inner mesh throughout the entire geometry thereof. Preferably, the main network of channels will run through the inside of the disc.

The 3D network of interconnected micropores which form microchannels serves the function of facilitating the cellular invasion and neoformation of the soft tissues (dermal and adipose) inside the collar. Since the silicone alone does not promote protein adsorption and optimal cellular adhesion on a molecular level, the bond that is produced is mainly mechanical due to the interconnection of the pores which causes the tissue to interconnect with itself through said microchannels.

With the objective of creating a chemical bond which is stronger and more stable on a molecular level than the one produced solely by the material of the disc, it is proposed that either an internal Ti mesh or a polymer that is bioactive or coated with a bioactive material (for example hydroxyapatite) which produces said molecular bond be used. In order to improve the adhesion of the tissues to said mesh it is proposed that the network of main channels which surround the internal mesh throughout the entire geometry thereof be generated. Thus, a larger contact surface is facilitated between tissues and internal mesh increasing the amount of tissue adhered thereto and therefore the bond strength. This main network of channels, together with the internal mesh and the arrangement of the tissues, in turn reduces the intussusception of the epidermal tissue since it offers a physical limit to the growth of the dermis.

The fastening of the mesh to the ring can be done using pressure, crimping in holes of the ring or by means of a hoop threaded onto the body of the ring.

To fasten and adjust the position of the collar, the device can comprise at least one washer arranged in the carrier element on the side of the collar next to the bone, and a lock nut on the opposite side. Preferably, a sealing O-ring will be arranged between the lock nut and the collar.

All the materials of the invention will be biocompatible as implicitly required by the use thereof.

DESCRIPTION OF THE DRAWINGS

The following figures are included for a better understanding of the invention.

EMBODIMENTS OF THE INVENTION

Figure 1:
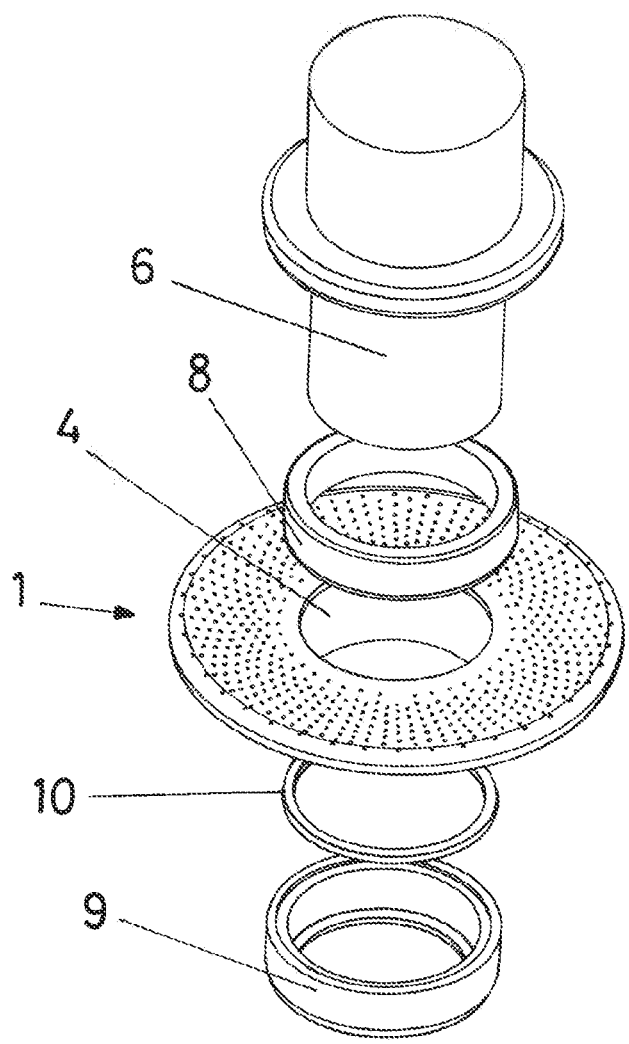
FIG. 1: exploded view of an exemplary embodiment of the invention.

Below an embodiment of the invention will be briefly described, as an example by way of illustration and not limitation thereof.

The device of the invention comprises several differentiated elements, the main one being a percutaneous collar (1) which has a flexible internal grate or mesh (2) made of, for example, titanium or a polymeric material coated or not with a material which favours dermal adhesion, inside a disc (3) made of microporous silicone or similar and a rigid internal ring (4) intended to create a firm and stable seal with the epidermis (5). Preferably, the ring (4) will comprise internal threading to facilitate the placement in a carrier element (6), which could be a rod or a catheter, also threaded, wherein the assembly of the device is assembled.

The position of the collar can be adjusted in order to adapt to the thickness of the adipose tissue (7) with the goal of adapting to the variability existing between different subjects and amputated limbs. The collar (1) is adjusted in height in the carrier element (6) by means of a washer (8) available with different heights, or by means of several washers (8), the sum of which offers the height desired. This washer (8) acts as an regulating block for the percutaneous collar (1). In order to ensure the fastening of the collar (1), a pressure lock nut (9) is designed which is threaded onto the distal end of the percutaneous area of the carrier element (6), remaining outside the body. A sealing O-ring (10) is inserted between the collar (1) and the pressure lock nut (9), which can be coated with a germicidal material, responsible for preventing the proliferation of bacteria inside.

Since the systems integrating a percutaneous collar (1) are sensitive to the relative positions that the soft tissues have with respect to the collar (1), the percutaneous portion of the device is adjustable in height and able to be adapted to the thickness of the adipose tissue or other soft tissues and, in the case of osteotomies, to the final distance between the level of osteotomy performed and the epidermis.

Figure 2:
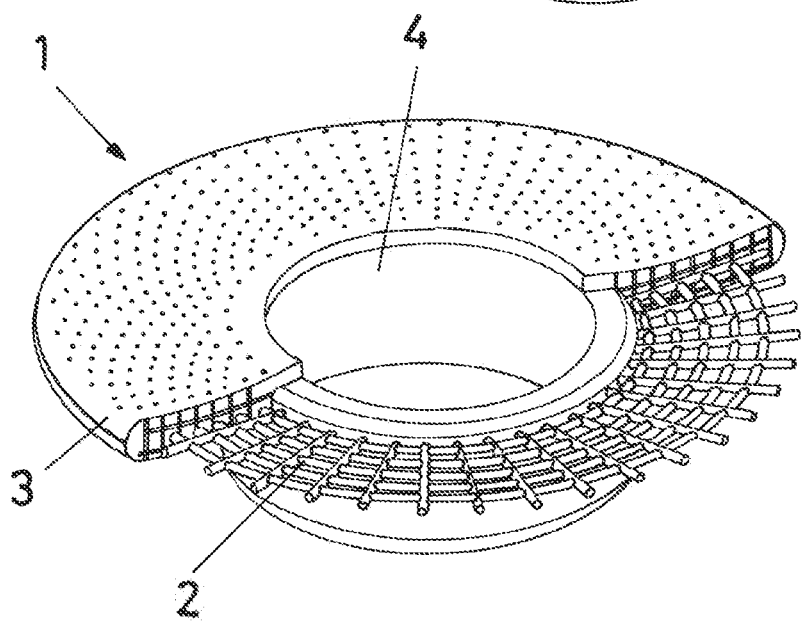
FIG. 2: view of an exemplary embodiment of the percutaneous collar wherein a portion of the disc has been withdrawn, as well as a detail view.
Figure 2:
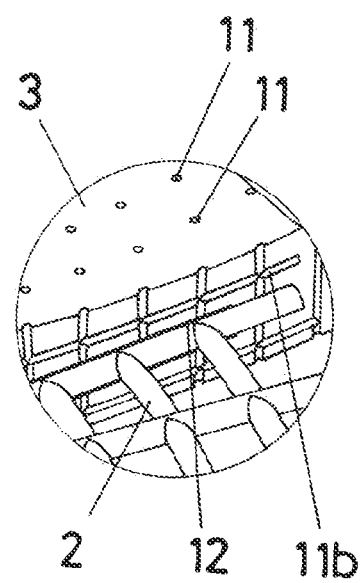
Figure 3:
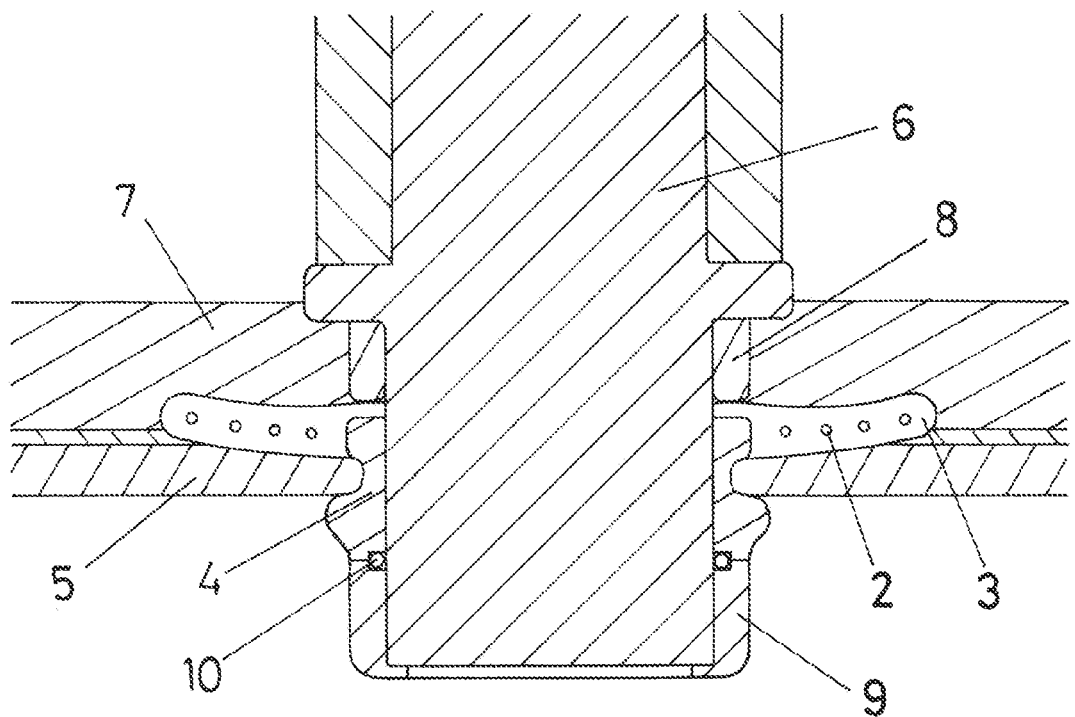
FIG. 3: side view of an exemplary embodiment implanted in an amputated extremity or limb.

The internal mesh (2) proposed to favour the adhesion of the dermal and adipose tissue thereto limiting the marsupialisation is protected by the disc (3) made of a flexible material (silicone or similar) with interconnected micropores which form microchannels favouring the guided internal growth of the precursor cells of the scar tissue through a three-dimensional micropore structure (11b) connected in FIG. 2 to the surface micropores (11) and to the main network of channels (12) surrounding the internal mesh. The combination of both materials equips the area of the collar (1) in contact with the soft tissues with a structural rigidity such that it is able to support the weight of said tissues while adapting to the movements thereof, absorbing the tearing tensions due to pulling or falls, generated in the vicinity of the bond of the percutaneous collar (1) with the dermal tissue and the distal soft tissues.

As seen in the figures, the microchannels formed by interconnected micropores (11b) are accessible from the outside of the collar (1), while the ordered channels (12) have the same or larger cross section and are preferably completely contained in the collar (1), that is, they do not reach the exterior thereof. To do so, the preferred shape of the ordered channels (12) follows the geometric distribution of the internal mesh, while the microchannels formed by the interconnected micropores (11b) have a random arrangement although by way of illustration in the figures they are shown as parallel.

Figure 4:
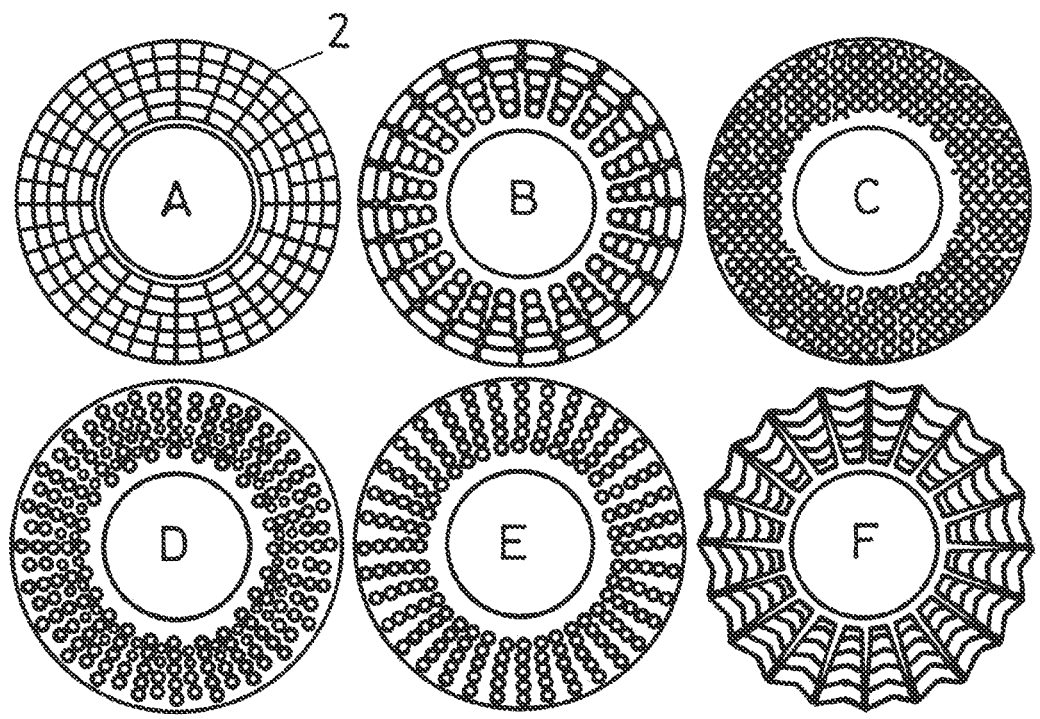
FIG. 4: several examples of geometry applicable to the internal mesh.

FIG. 4 shows several ways of making the mesh (2), whether it be from crossed longitudinal and radial elements, which form a spider web-type structure or plates with a plurality of holes. The variants like the ones shown in FIGS. 4A, 4B, 4C and 4F can vary the rigidity thereof by modifying the separation between radii or the cross section thereof. The meshes (2) similar to the ones in FIGS. 4D and 4E are adjusted depending on the size and number of holes, in addition to the thickness of the plate.

The preferred variant is the one shown in FIG. 4F, comprising a plurality of wave shapes in the plane of the disc, perpendicular thereto or in both directions, concentric and joined by a series of radii, such that the radii are joined with internal or external peaks of each shape, leaving internal holes in chevron. This variant has the best behaviour since it can support large deformations producing lower tensions in the concentric bars and distributing them in a more homogeneous manner.

The claims described below are part of the description and all the dependent claims are considered as included.

The invention claimed is:

1. A device for the exo-prosthetisation of limbs and other percutaneous applications comprising:

a carrier element for a percutaneous collar,
an element projecting from a epidermis,
a percutaneous collar formed by a central rigid ring joined to the carrier element,
a silicone disc comprising an outer portion which in turn comprises external micropores, and two external faces defining a volume between them,
an internal flexible mesh disposed inside the silicone disc, wherein the entire volume of the silicone disc comprises a three-dimensional network of interconnected micropores forming microchannels to favor the guided internal growth of the precursor cells of the scar tissue, wherein the three-dimensional network of interconnected micropores is connected to the external micropores and to a network of ordered channels surrounding the internal mesh, so that said interconnected micropores are accessible from the outside of the collar while the ordered channels do not reach the exterior thereof.

2. The device of claim 1, wherein the interconnected micropores of the three-dimensional network have a random arrangement.

3. The device of claim 1, wherein the central rigid ring is configured to be threaded to the carrier element.

4. The device of claim 1, wherein the internal flexible mesh is surrounded by a network of ordered channels following a geometric distribution of the internal flexible mesh.

5. The device of claim 4, wherein the network of ordered channels runs through the inside of the silicone disc of the percutaneous collar.

6. The device of claim 1 further comprising at least one washer on the side of the percutaneous collar close to a bone in order to adjust the final position of the percutaneous collar, and a lock nut on the opposite side.

7. The device of claim 6, further comprising a sealing O-ring between the lock nut and the percutaneous collar.

8. The device of claim 1, wherein the internal flexible mesh is made of metal or a polymer coated in titanium, hydroxyapatite or a bioactive material.

9. The device of claim 1, wherein the carrier element is a catheter for percutaneous applications such as ostomies such as cystostomies or colostomies, or gastric applications.

10. The device of claim 1, wherein the carrier element is an intramedullary rod.

11. The device of claim 1, wherein the internal flexible mesh comprises a plurality of wave shapes that are concentric and joined by a series of radii, leaving internal holes in chevron.

* * * * *